United States Patent [19]
De Faria-Correa et al.

[11] Patent Number: 5,533,496
[45] Date of Patent: Jul. 9, 1996

[54] ENDOSCOPIC TECHNIQUE PARTICULARLY SUITED FOR EXPLORATORY SURGERY

[75] Inventors: Marco A. M. De Faria-Correa, Rio Grande Do Sul, Brazil; Julio Hochberg, Morgantown, W. Va.

[73] Assignee: Very Inventive Physicians, Inc., Tucson, Ariz.

[21] Appl. No.: 196,712

[22] Filed: Feb. 15, 1994

[51] Int. Cl.$^6$ .................................................. A61B 1/012
[52] U.S. Cl. ........................ 128/898; 600/157; 600/169
[58] Field of Search ........................ 128/4–10; 604/164

[56] References Cited

U.S. PATENT DOCUMENTS

| | | | |
|---|---|---|---|
| 3,494,354 | 2/1970 | Yokota et al. | 128/6 |
| 4,076,018 | 2/1978 | Heckele | 128/6 |
| 4,770,653 | 9/1988 | Shturman | 128/6 X |
| 4,819,620 | 4/1989 | Okutsu | 128/4 |
| 5,271,380 | 12/1993 | Riek et al. | 128/4 |

FOREIGN PATENT DOCUMENTS 4133073  4/1992  Germany ................................. 128/6

*Primary Examiner*—Richard J. Apley
*Assistant Examiner*—John P. Leubecker
*Attorney, Agent, or Firm*—Ogram & Teplitz

[57] ABSTRACT

Improved exploratory, pre- and post- surgical techniques are now available due to an improved endoscope which uses a housing with a window member thereon. Due to the window's angle and the air-pocket between the viewing tip of the endoscope and the window, exceptional vision is provided without the need to create artificial chambers within the body. Should the window become occluded with debris, the surgeon can easily clean the window by wiping it against a nearby organ or muscle to dislodge the debris. Since no inflating gas is used, techniques employing the endoscope create minimal trauma and are ideally suited for exploratory surgery, pre-surgical inspection of the operation site, and post-surgical inspection to assure the operation obtained the desired results.

18 Claims, 2 Drawing Sheets

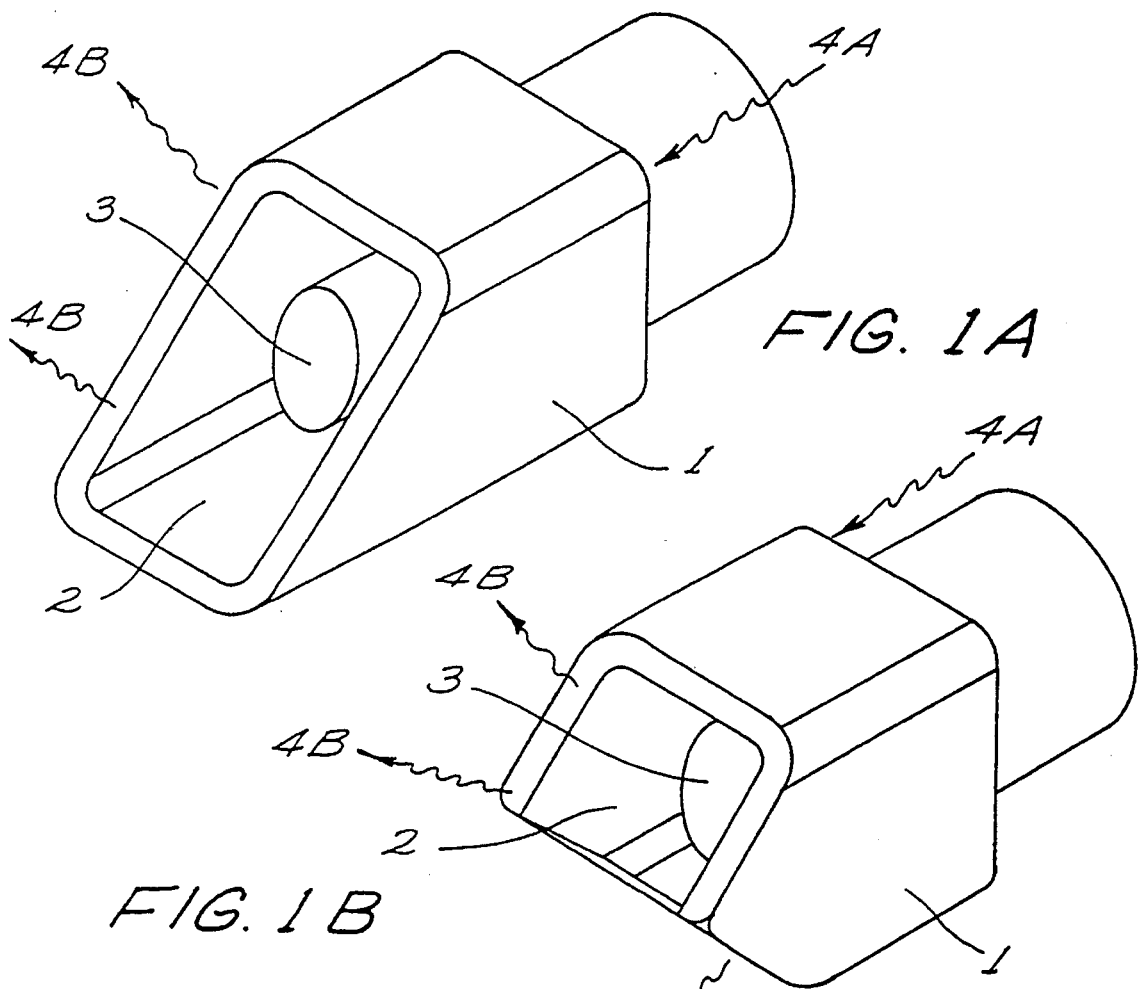
FIG. 1A
FIG. 1B
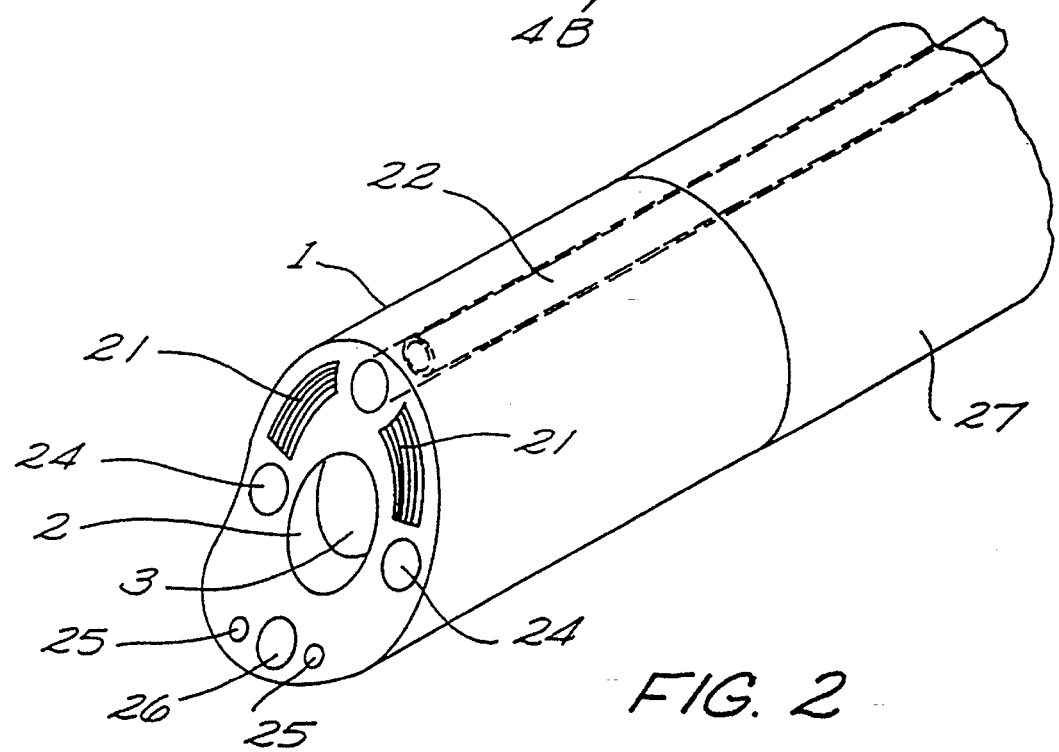
FIG. 2

ENDOSCOPIC TECHNIQUE PARTICULARLY SUITED FOR EXPLORATORY SURGERY

BACKGROUND

This invention relates generally to surgical tools and techniques and more particularly to endoscopic techniques and equipment.

Endoscopes permit the physician to view inside the patient with a minimum of trauma to the patient. A modern endoscope utilizes fiber optics and a lens mechanism to capture an image from the end of the tube and carry the image back to the surgeon or video monitor. Illumination at the site of the viewing end is provided by a fiber optic transmission of light to the end. Periodically, a washing action is carried out to clean the viewing optics from body debris which may collect on the lens system.

Endoscopic viewing requires only a minimal of trauma to the patient due to the small size of the endoscope. A wide range of applications have been developed for the general field of endoscopes including: Cystoscope—for the bladder; Bronchoscope—for the Bronchi; Gastroscope—for the esophagus, stomach, and duodenum; Colonscope—for the colon; laparoscope—for the abdominal cavity; and arthroscope—for the knee joint. Within this discussion, endoscopy is intended to include all of these applications and other similar type of procedures.

Endoscopic surgical techniques have been used in General Surgery, Gynecology, Orthopedics, and its advantages over the traditional surgical techniques have been shown in these different fields. These advantages include: a more comfortable position to the surgeon (thereby reducing fatigue during an extended operation); the amplification of images seen in the video monitor (better visualization of the site); safer (reduced body fluid exposure to the health-care team); less trauma to the patient; and, delicate procedures can be performed through extremely small incisions (faster recuperation and reduced scaring). All of these advantages are desirable in all fields of surgery and are particularly advantageous in the field of cosmetic plastic surgery.

Generally, video-endoscopic techniques have been developed for inner cavities and anatomical spaces that can be expanded by gases (peritoneal and pleural cavities) because the endoscope requires a work space between the optical system and the tissues for the purposes of illumination, capture of images, and execution of procedures.

Working at the subcutaneous tissue, the surgeon must cut many blood vessels which travel between the to-be-separated layers by the expansion of gas. This is a dangerous step due to the a risk of gas embolization, dispersion, and toxicity.

It is clear that there is a continuing need to reduce the trauma and danger associated with the endoscope so as to expand the endoscope's range of application.

SUMMARY OF THE INVENTION

The invention is an improved endoscope assembly for exploratory surgery which permits exceptional vision while eliminating the requirement of both washing of the lens or expansion of the body cavity. Using a standard endoscope, a housing is placed over the end of the endoscope. The housing is equipped with a window for viewing through by the endoscope's viewing tip. The window is arranged at an angle different from the angle of the viewing tip to eliminate back-scattering of light from the endoscope which might degrade the endoscope's vision. An air-chamber between the viewing tip of the endoscope and the window assures the crispest vision possible.

Further, fogging of the window is eliminated through the use of heating wires, dry gases, or the like so that the endoscope is also useful for cadaver use by medical students.

Because of the improved clarity, due to the back-scattering elimination and the air-chamber, the endoscope is used without either the aid of washing or the expansion of the body cavity. The reduced trauma (no inflation) associated with the improved endoscope permits the endoscope to be used for exploratory surgery in such areas as emergency room trauma diagnosis as well as pre- and post-operative inspection of the patient.

This device is a medical surgical instrument to be used in endoscopic plastic surgery and allows work at the subcutaneous tissue level through one extremely small incision. The use of any gas is totally eliminated since the housing creates its own work space, thereby totally avoiding any risk of gas embolism.

In one embodiment of the invention, the device is a surgical instrument used to perform endoscopic surgery in the subcutaneous tissue. Its workhead can perform a variety of functions including: visualization, irrigation, aspiration, cutting or cauterization, and placement of instrumentation in the subcutaneous tissue. In this embodiment, the various tools already discussed are passed through the housing member in which the window and air-chamber are located.

These endoscopic surgical tools, such as irrigation devices, aspiration devices, cutting and cauterization tools, and the like, are well known to those of ordinary skill in the art.

Since the air-chamber eliminates the need for inflating gases in the patient, and assures clear imaging, the endoscope is able to move anywhere without fear of causing undue trauma to the patient.

This instrument is a "workhead" like a capsule that also acts as a blunt/sharp dissector. The housing or workhead has a dissector portion that extends partially past the window permitting the surgeon to "pry" into various points of the subcutaneous tissue to either gain access or to selectively dissect the area.

The instrument so created creates a surgical tool especially suited for plastic surgery that:

(a) Avoids the risk of gas embolization and toxicity;

(b) Simultaneously, provides dissection and visualization;

(c) Brings to plastic surgery the advantages of minimal invasive surgery: less tissue trauma, decreased rates of infection, less hospitalization time, and small scars.

Perhaps the greatest power of this device is in the field of general exploratory surgery in which a diagnosis is sought. As example, often examination of a trauma victim requires a determination on if there has been any damage to the internal organs. Although some non-invasive testing may be done, often the physician requires a "look at" the suspect organ.

Using the present invention, a simple incision is made to gain access to the area of interest. The endoscope is inserted into the body and is maneuvered by the surgeon so that the organ or area of interest can be examined on the video screen displaying the scene from the endoscope's viewing tip.

Assume the physician suspects that there has been damage done to the kidney. Via an incision near the kidney, the endoscope is passed into the body. The kidney and its surrounding tissue are inspected for damage. Internally, there is normally little loose or free blood so no washing of the window is required. If an undue amount of blood is encountered, then the trauma physician knows that the kidney is bleeding and that a traditional operation is required.

During the process, if the window becomes occluded due to debris lodging on the window, the surgeon simply "wipes" the window against any nearby organ to dislodge the debris and "clear-up" the viewing.

The same technique is also available for a surgeon to explore a site before traditional operative techniques are employed. This gives the surgeon an advanced view of the site so that the surgeon is fully prepared for what may be encountered.

Similarly, a post-operative patient can be examined to assess the results of the surgery. As example, the surgeon is able to determine if the internal stitches are holding and if there is any seepage.

For general exploratory surgery the instrument is especially useful since:

(a) No inflating gasses are used on the patient;

(b) No washes are required since the window stays particularly clean permitting a "dry" examination to be made; and, (c) Trauma to the patient is reduced to a minimum with the only incision being the entry incision for the endoscope.

The invention, together with various embodiments thereof will be more fully explained by the accompanying drawings and the following descriptions thereof.

DRAWINGS IN BRIEF

FIGS. 1A and 1B are perspective views of two embodiments of the invention, an attachment for an endoscope.

FIG. 2 is a perspective view of an enhanced embodiment of the invention.

Figure 3A:
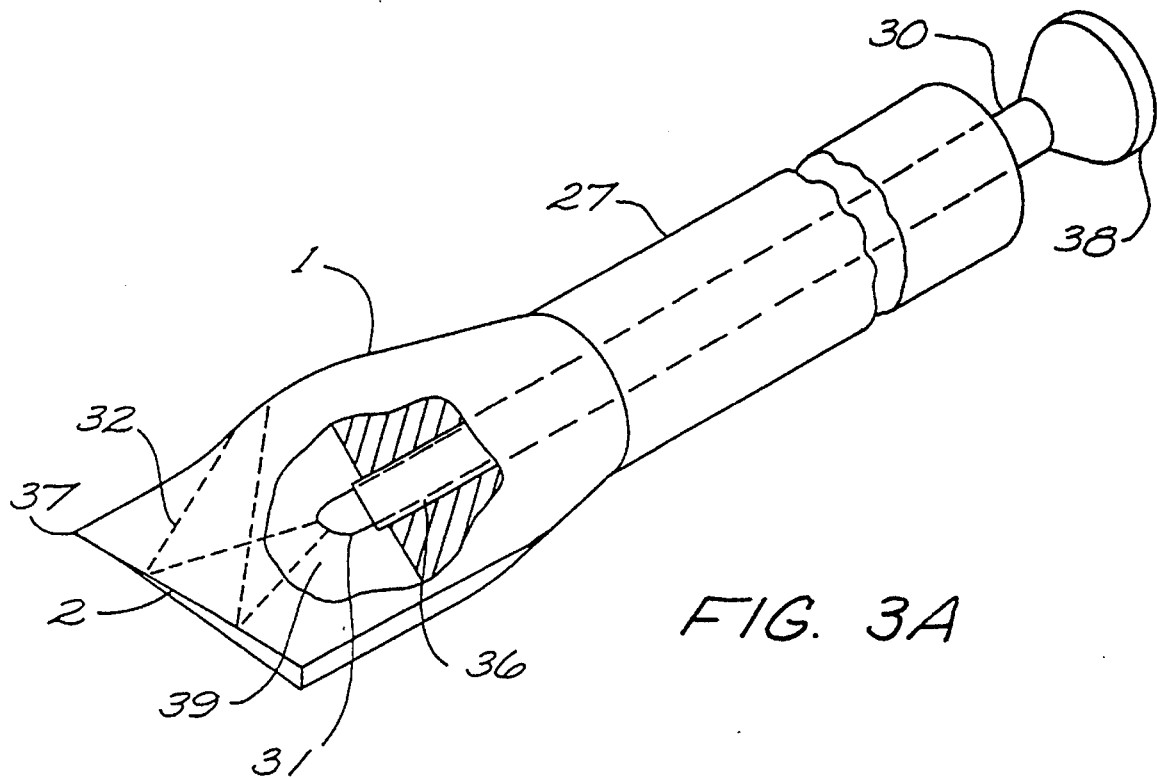
Figure 3B:
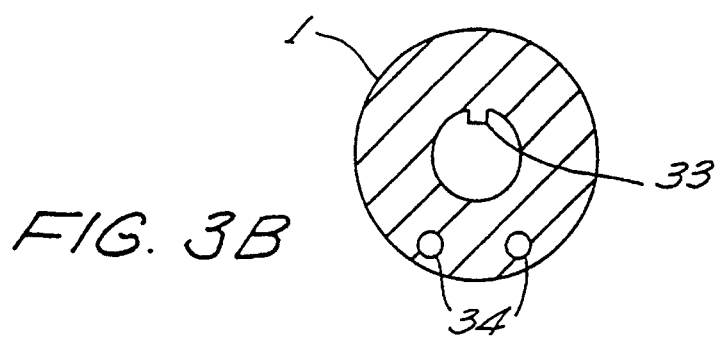
Figure 3C:
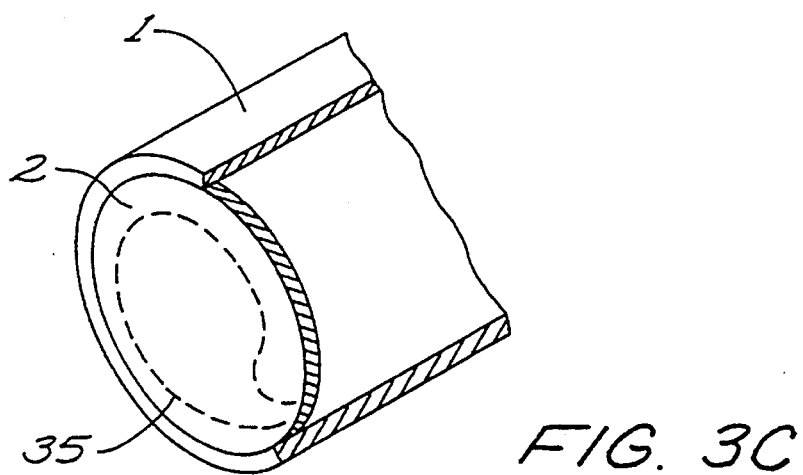

FIGS. 3A, 3B, and 3C are different views of the preferred embodiment showing the entire endoscope, the key and venting mechanism, and a wire heating element for the window respectively.

DRAWINGS IN DETAIL

FIGS. 1A and 1B are perspective views of two embodiments of the invention, an attachment for an endoscope.

As noted, this invention is a medical surgical instrument for endoscopic plastic surgery which eliminates the need for inflatable gas, thus avoiding the risk of gas embolization. Housing 1 is attached through a variety of means either directly onto the endoscope's tube or via a cannula (not shown) which is affixed to the tube of the endoscope. Opening 3 communicates with a channel in the housing 1 to provide an opening for the viewing tip of the endoscope (not shown). Once in place, the viewing tip of the endoscope is directed to view through window 2 into the proximate tissue area.

Between opening 3 and window 2 is an air-chamber which provides a "mask" type of effect so that clarity of vision is maintained. The air-chamber works in the same manner as a swimmer's mask, keeping liquids and materials away from the lens so that a clear focus is obtainable. This air-chamber permits the lens of the endoscope to work optimally and obtain a clear view through the window.

Note that the angle of window 2 is different from the angle of the viewing tip of the endoscope. As example, if the viewing tip has an angle of 30 degrees, then the window's angle must be anything but 30 degrees (the preferred angle is 45 degrees for the window). This differing of the angle keeps the viewing lens and the window from being parallel. Should the two be parallel, then light from the endoscope reflects off the interior of the window back into the lens and degrades the resulting image. As it is in this invention, with differing angles, light from the endoscope that does not pass through the window, is reflected back into the housing and not into the endoscope's viewing tip. A further enhancement to the apparatus is to coat the interior of housing 1 with a light absorbing material such as black paint to totally eliminate any back-scattering degradation of the image.

An endoscope equipped with this mask apparatus is ideally suited for exploratory surgery since the surgeon is able to direct the viewing tip to wherever is of concern without having to use any inflating gas or even any liquid to wash the window. Clear inspection is assured by the air-chamber enhancement of the optics and the entire inspection is essentially "dry" except for the natural fluids within the body.

If blood is encountered in the exploratory phase, indicating internal bleeding, then traditional surgery is warranted to correct the internal bleeding.

Should window 2 become occluded with debris, then the surgeon can easily clean the window by "wiping" the window against a nearby organ or muscle to dislodge the debris.

An important aspect of the present invention is its ability to accommodate a variety of illumination sources. In the embodiments of FIGS. 1A and 1B, housing 1 is preferably constructed of acrylic plastic which permits the transmission of light, 4A, to the edges around window 2 which will thus illuminate the work-area as shown by arrows 4B. In this manner, light is communicated around the work site and avoids any problems of back-scattering which might occur.

The shape of housing 1 is also beneficial as illustrated with FIG. 1A. Due to the wedge shape, housing 1 is slid between subcutaneous layers until housing 1 is in the proper location. By rotating housing 1 one hundred eighty degrees (putting the wedge on the other side), the subcutaneous layer is pried apart creating an enhanced cavity for viewing. This micro-cavity causes minimal trauma to the patient yet permits the surgeon to obtain exception viewing capacity and, as shown later, a micro area for surgical work.

FIG. 2 is a perspective view of an enhanced embodiment of the invention. This embodiment is particularly useful for a full range of surgical applications.

Housing 1 is attached to cannula 27 via a screw mechanism or other suitable means. A screw mechanism is preferred since it permits easy disassembly for post-operative sterilization.

In this embodiment a variety of orifices are provided for traditional endoscopic surgical tools including: an optical system opening 24; illumination source opening 21; irrigation source opening 26; an aspiration source opening 25; instrumentation channels source to cut, cauterize, and sutures opening; and elevators/retractors channels source opening 22. Tools for these various functions are well known to those of ordinary skill in the art. This embodiment utilizes these established endoscopic surgical tools.

This tool permits these various endoscopic surgical tools to be carried to the workspace at the subcutaneous tissue level without the use of gas to create a viewing chamber; this is provided by the housing's air-chamber.

Further, the housing itself provides for a blunt dissector which is wedged into the area of interest and then withdrawn for the performance of the work by the endoscopic surgical tool. Because of the improved viewing created by window 2, no gas or expansion of the workspace is required.

Note that an elevator/retractor is inserted through opening 22 to move tissue away from the apparatus and provide a micro-work-site for the other endoscopic tools. As discussed before, trauma is reduced permitting the patient faster recuperation and less possibility of collateral damage.

Optical system 24 provides stereoscopic vision which can be used either in conjunction with or in lieu of the endoscopic viewing tip which extends through an orifice. Stereoscopic vision gives the surgeon a feeling for depth and as such permits more delicate surgery to be performed.

FIGS. 3A, 3B, and 3C are different views of the preferred embodiment showing the entire endoscope, the key and venting mechanism, and a wire heating element for the window respectively.

As shown in FIG. 3A, endoscope 30 has at one end viewing tip 31 and at the other end, eyepiece 38 through which the surgeon views the site. Those of ordinary skill in the art recognize that in lieu of eyepiece 38, a video hook-up and screen could be substituted. Endoscope 30 is inserted through cannula 27 such that a portion of the endoscope's tube is retained by channel 36, thereby positioning viewing tip 31 correctly in the air-chamber 39 and viewing through window 2.

Light from viewing tip 31 which is diffracted from window 2, as shown by 32, impinges onto the interior of housing 1 and is absorbed therein by a light absorbing material (not shown). In this manner, diffracted light is not permitted to affect the visual acuity of the endoscope. Diffracted light 32 is directed away from viewing tip 31 by controlling the angle of window 2 and the angle of viewing tip 31 such that the two angles are not equal to each other. This assures the redirection of diffracted light 32 away from viewing tip 32.

Dissector 37 located on housing 1 permits the easy movement of the assemblage through the patient. In the preferred embodiment of dissector 37, a portion of the dissector 37 is blunt while another portion is sharp; thereby permitting the surgeon the choice of either a blunt or sharp dissector.

Viewing tip 31 and window 2 are kept in proper alignment in this embodiment through the use of key 33 as shown in FIG. 3B. Key 33 mates with a notch on endoscope 30 (now shown) thereby eliminating rotation of endoscope 31 relative to window 2.

Channels 34 are also created in this embodiment to communicate defogging mechanisms to window 2. In this embodiment, wire 35 is embedded in window 2 (FIG. 3C) permitting window 2 to be heated for defogging.

Other defogging techniques are well known to those of ordinary skill in the art including the passage of a dry gas (heated or not) through opening 34 to remove any water vapor which may be present in air-chamber 39.

Defogging is not usually necessary when doing exploratory surgery since the surrounding medium, the patient, is warm. When this apparatus is used as a teaching tool for medical students, defogging becomes critical due to the cold nature of the cadaver which encourages fogging of window 2.

It is clear from the foregoing that the present invention creates a vastly improved endoscope and apparatus, permitting surgical techniques which were heretofore unavailable.

What is claimed is:

1. An exploratory surgery technique comprising the steps of:
   a) creating an incision for access to a site of interest;
   b) inserting an endoscope having a housing enclosing a viewing tip of said endoscope, said housing having a window member and an air-chamber between said viewing tip and said window member, through said incision;
   c) maneuvering said window to a position proximate to said site of interest; and,
   d) periodically cleaning said window member by wiping said window member against an internal organ.

2. The exploratory surgery technique according to claim 1 further including the step of periodically defogging said window member.

3. The exploratory surgery technique according to claim 2 wherein the step of periodically defogging said window member includes the step of providing an electrical charge to a heating wire embedded in said window member.

4. The exploratory surgery technique according to claim 2 wherein the step of periodically defogging said window member includes the step of directing a stream of dry gas against an interior side of said window member.

5. The exploratory surgery technique according to claim 2 wherein the step of maneuvering said window includes the step of dissecting, via said housing, tissue in a path of said housing.

6. A pre-surgical technique comprising the steps of:
   a) prior to a surgical operation:
      1) creating an incision for access to a site of the operation,
      2) inserting an endoscope having a housing enclosing a viewing tip of said endoscope, said housing having a window member and an air-chamber between said viewing tip and said window member, through said incision,
      3) exploring the site of the operation with said endoscope, and,
      4) periodically cleaning said window member by wiping said window member against an internal organ; and,
   b) performing said surgical operation.

7. The surgical technique according to claim 6 further including the step of periodically defogging said window member.

8. The surgical technique according to claim 7 wherein the step of periodically defogging said window member includes the step of providing an electrical charge to a heating wire embedded in said window member.

9. The pre-surgical technique according to claim 7 wherein the step of periodically defogging said window member includes the step of directing a stream of dry gas against an interior side of said window member.

10. The pre-surgical technique according to claim 7 wherein the step of maneuvering said window includes the step of dissecting, via said housing, tissue in a path of said housing.

11. A post-surgical technique comprising the steps of:
   a) after a surgical operation of a patient, inserting an endoscope having a housing enclosing a viewing tip of said endoscope, said housing having a window member and air-chamber between said viewing tip and said window member, into said patient;
   b) exploring the site of the operation with said endoscope for abnormalities;

c) periodically cleaning said window member by wiping said window member against an internal organ; and, d) removing said endoscope from said patient.

12. The post-surgical technique according to claim 11 further including the step of periodically defogging said window member.

13. The post-surgical technique according to claim 12 wherein the step of periodically defogging said window member includes the step of providing an electrical charge to a heating wire embedded in said window member.

14. The post-surgical technique according to claim 12 wherein the step of periodically defogging said window member includes the step of directing a stream of dry gas against an interior side of said window member.

15. The post-surgical technique according to claim 12 wherein the step of maneuvering said window includes the step of dissecting, via said housing, tissue in a path of said housing.

16. A health care giver's training technique comprising the steps of:

a) creating an incision in a cadaver;

b) inserting an endoscope having a housing enclosing a viewing tip of said endoscope, said housing having a window member and an air-chamber between said viewing tip and said window member, through said incision; and, c) exploring a site within said cadaver with said endoscope by,
1) dissecting, via said housing, tissue in a path of said housing,
2) periodically defogging said window member, and,
3) periodically cleaning said window member by wiping said window member against an internal organ.

17. The training technique according to claim 16 wherein the step of periodically defogging said window member includes the step of providing an electrical charge to a heating wire embedded in said window member.

18. The training technique according to claim 16 wherein the step of periodically defogging said window member includes the step of directing a stream of dry gas against an interior side of said window member.

* * * * *